United States Patent
Gouache et al.

(10) Patent No.: US 9,641,579 B2
(45) Date of Patent: May 2, 2017

(54) METHOD AND APPARATUS TO CONTROL A MULTIPATH ADAPTIVE STREAMING SESSION

(71) Applicant: Thomson Licensing, Issy de Moulineaux (FR)

(72) Inventors: Stephane Gouache, Cesson Sevigne (FR); Helmut Burklin, Cesson Sevigne (FR); Gilles Straub, Cesson Sevigne (FR)

(73) Assignee: Thomson Licensing DTV, Issy-les-Moulineaux (FR)

( * ) Notice: Subject to any disclaimer, the term of this patent is extended or adjusted under 35 U.S.C. 154(b) by 37 days.

(21) Appl. No.: 13/714,347

(22) Filed: Dec. 13, 2012

(65) Prior Publication Data

US 2013/0151673 A1 Jun. 13, 2013

(30) Foreign Application Priority Data

Dec. 13, 2011 (EP) .................................... 11306642

(51) Int. Cl.
*G06F 15/16* (2006.01)
*H04L 29/06* (2006.01)

(52) U.S. Cl.
CPC .......... *H04L 65/60* (2013.01); *H04L 65/4084* (2013.01); *H04L 65/605* (2013.01); *H04L 65/80* (2013.01)

(58) Field of Classification Search
CPC ........ H04L 65/60; H04L 65/80; H04L 67/32; H04L 65/601; H04L 65/607; H04L 67/2823; H04L 51/06; G06F 17/30053

(Continued)

(56) References Cited

U.S. PATENT DOCUMENTS 7,051,275 B2 * 5/2006 Gupta .................. G06F 17/241
707/E17.009
7,423,649 B2 * 9/2008 Henocq .................. G06T 13/80
345/473

(Continued)

FOREIGN PATENT DOCUMENTS

| CN | 1620656 A | 5/2005 |
|---|---|---|
| WO | 2010/090732 A1 | 8/2010 |
| WO | 2010/148048 A1 | 12/2010 |
| WO | WO2011015243 | 2/2011 |
| WO | 2011/101371 A1 | 8/2011 |
| WO | 2011/109101 A1 | 9/2011 |

OTHER PUBLICATIONS

European Search Report dated Jul. 4, 2012.

(Continued)

*Primary Examiner* — Kristie Shingles
(74) *Attorney, Agent, or Firm* — Myers Wolin, LLC

(57) ABSTRACT

The present invention concerns a method to control the transmission and transmission data rate between at least two servers and a receiver. The servers being adapted to transmit data representative of an audiovisual content. The audiovisual content being available from each of said at least two servers in at least two versions. The versions corresponding respectively to different transmission bit-rates. The servers being adapted to transmit audiovisual contents in successive parts, each of said successive parts being chosen as one of at least two versions in response to transmission requests sent by the receivers, said transmission requests comprising a transmission parameter.

19 Claims, 6 Drawing Sheets

(58) Field of Classification Search
USPC .................................................. 709/219, 217
See application file for complete search history.

(56) References Cited

U.S. PATENT DOCUMENTS

| | | | |
|---|---|---|---|
| 7,620,687 | B2 | 11/2009 | Chen et al. |
| 7,797,426 | B1 | 9/2010 | Lyon |
| 8,155,090 | B2* | 4/2012 | Ramesh et al. ............... 370/336 |
| 8,681,680 | B2* | 3/2014 | Mao et al. .................... 370/312 |
| 8,874,777 | B2* | 10/2014 | Ma ..................... G06Q 30/0241 370/486 |
| 8,880,587 | B2* | 11/2014 | Cobb .................... H04L 65/605 709/203 |
| 8,965,180 | B2* | 2/2015 | Knight ................. G11B 27/034 386/282 |
| 9,009,251 | B1* | 4/2015 | Sanjeev ........... G06F 17/30905 709/217 |
| 2002/0027616 | A1 | 3/2002 | Jun et al. |
| 2003/0093515 | A1 | 5/2003 | Kauffman |
| 2010/0036954 | A1 | 2/2010 | Sakata et al. |
| 2011/0082924 | A1 | 4/2011 | Gopalakrishnan |
| 2011/0122063 | A1* | 5/2011 | Perlman .................. A63F 13/12 345/161 |
| 2011/0188439 | A1* | 8/2011 | Mao et al. .................... 370/312 |
| 2011/0289189 | A1* | 11/2011 | Bartholomew ... G06F 17/30053 709/217 |
| 2012/0311094 | A1* | 12/2012 | Biderman .............. H04N 5/783 709/219 |

OTHER PUBLICATIONS

Ghareeb et al., "Performance Evaluations of a QoE-Based Multipath Video Streaming Mechanism over Video Distribution Network (VDN)", FMN 2009, LNCS 5630, Springer-Verlag Berlin Heidelberg Copyright 2009, pp. 236-241.

Jurca et al., "Distributed Media Rate Allocation in Multipath Networks", Signal Processing Institute Technical Report, TR-ITS-2006.009, Sep. 14, 2006.

Jurca et al., "Video Packet Selection and Scheduling for Multipath Streaming", IEEE Transactions on Multimedia, vol. 9, No. 3, Apr. 2007, pp. 629-641.

Shui et al., "Video Streaming Transmission Over Multi-channel Multi-path Wireless Mesh Networks", IEEE Copyright 2008.

Broadband Forum Technical Report, TR-069 "CPE WAN Management Protocol v1.1" Version: Issue 1 Amendment 2, Version Date: Dec. 2007.

Tsai et al., "Multi-path transmission control scheme combining bandwidth aggregation and packet scheduling for real-time streaming in multi-path environment", IET Communications, 2010, vol. 4, Iss. 8, Received Oct. 15, 2009, Revised Dec. 2, 2009, pp. 937-945.

Gouache et al., "Distributed & Adaptive HTTP Streaming", Proceedings of the 2011 IEEE International Conference on Multimedia and Expo, pp. 1-7, Barcelona, Spain, Jul. 11-15, 2011.

First Office Action issued by the State Intellectual Property Office of China for corresponding Chinese Patent Application No. 201210538808.6, dated Dec. 5, 2016, with an English translation.

* cited by examiner

METHOD AND APPARATUS TO CONTROL A MULTIPATH ADAPTIVE STREAMING SESSION

This application claims the benefit, under 35 U.S.C. §119 of EP Patent Application 11306642.7, filed 13 Dec. 2011.

FIELD OF THE INVENTION

The present invention relates generally to video streaming content distribution and in particular to a remote management of receivers when many servers are collaborating in a multipath streaming session.

BACKGROUND OF THE INVENTION

This section is intended to introduce the reader to various aspects of art, which may be related to various aspects of the present invention that are described and/or claimed below. This discussion is believed to be helpful in providing the reader with background information to facilitate a better understanding of the various aspects of the present invention. Accordingly, it should be understood that these statements are to be read in this light, and not as admissions of prior art.

Streaming is the process where the content consumed by a client is sent in small pieces to it as opposed to downloading where the whole multimedia file is transferred to the client before the rendering.

Existing streaming protocols include RTP/MPEG TS/UDP and more specifically HTTP.

HTTP streaming is a technology recently advertised by Apple with its iPhone and by Microsoft with its Smoothstreaming that is gaining popularity thanks to its ability to leverage the existing Content Delivery Network (CDN) infrastructure. Moreover standardized solutions are now proposed in 3GPP and are under preparation in MPEG.

A CDN is a system of computers containing copies of data, located at various nodes of a network so as to maximize bandwidth for access to the data from clients throughout the network.

The adaptive HTTP streaming based on a prepared media content split in several segments encoded at different bit-rates, is able to offer a satisfactory quality by leveraging the existing CDN infrastructure.

This solution is very practical for making short events (sports, concerts, online training etc.) available through adaptive streaming since the CDN infrastructure can simply be rented for the duration of the event. However, for longterm deployments or when making a large number of contents available, the operating cost of a CDN infrastructure becomes significant and may simply be unaffordable.

Recently there have been several companies trying to provide a CDN aggregation service. The concept they offer is quite simple. The content to serve is provisioned to the aggregation service together with a CDN usage policy defined by the customer. The actual delivery of the content is delegated to a number of simple CDN service providers whose usage is balanced to reflect the customer's policy. Since different CDN providers have different coverage, quality and pricing, the promise of CDN aggregators is to allow the customer to load-balance the usage of multiple CDN providers and thus to control the performance and delivery costs.

In all cases however, the load-balancing occurs at the instant when the end-user connects to the service, that is, an end-user already connected to the service will not be migrated from one CDN to the other. This may not be relevant when serving a e-commerce website but is a significant limitation for streaming since adaptive HTTP streaming often relies on a persistent TCP connection. Since the load-balancing mechanism operates at client admission time, the users redirected to a good quality CDN will experience a good quality service, whereas the users redirected to a less good quality CDN will experience a bad service with no chance of switching over to a better CDN. Similarly, if at some point in time the streaming service provider's policy is to turn off a given CDN for instance to reduce the operating costs, it will be difficult to migrate the currently connected end-users. More generally, delegating the load-balancing decision to the CDN aggregator with a couple of coarse policies significantly reduces the ability of the service provider to make its service fair and consistent over time from its end-users's perspective.

SUMMARY OF THE INVENTION

The present invention attempts to remedy at least some of the concerns connected with bandwidth sharing in the adaptive streaming in the prior art by providing a handling of the bandwidth sharing between many servers and many receivers receiving streaming contents.

In particular, the invention leveraging multipath streaming allows the controlling of a streaming service by balancing the amount of data being pulled from each of the CDN servers by the individual end-users receivers.

Certain aspects commensurate in scope with the disclosed embodiments are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

The invention concerns a method to control the transmission between at least two servers and a receiver, the servers being adapted to transmit data representative of an audiovisual content, the audiovisual content being available from each of the at least two servers in at least two versions, the versions corresponding respectively to different transmission bit-rates, the at least two servers being adapted to transmit the audiovisual content in successive parts, each of the successive parts being chosen as a part of one of at least two versions from one of at least two servers in response to transmission requests sent by the receiver, the transmission requests comprising at least a transmission parameter, the method comprising at a controller the steps of:

reception of information from a receiver, the information being representative of the delivery of an audiovisual content from one of at least two servers to the receiver, transmission of a control parameter to the receiver, the control parameter being computed from at least information in order to define from the control parameter at least one transmission parameter.

According to an embodiment of the invention, information is one of the following parameters:

a server identifier,
a receiver identifier,
an identifier of a group of receivers which comprises the receiver,
a positioning information of the receiver,
the data transmission bit-rate between any of at least two servers and the receiver,
a size of a data reception buffer of the receiver, a quality indicator of the delivery of the audiovisual content from one of at least two servers to the receiver, the number of times the receiver switches from one of the versions to another one of the versions during a given time interval while receiving the audiovisual content from one of at least two servers, the number of bytes received by the receiver from one of at least two servers during a predefined time interval, the number of bytes received by the receiver from one of at least two servers during a predefined time range for each of at least two versions of the audiovisual content.

According to an embodiment of the invention, the control parameter is one of the following parameters:

a server identifier, a maximum value of bit-rate to be requested to any of at least two servers, a list of allowed versions of the versions to be requested to any of at least two servers, a maximum size of reception buffer, a maximum speed factor to be indicated to any of at least two servers within the request, a parameter of the adaptive streaming algorithm of the receiver.

The invention also concerns an apparatus for receiving data, the data being representative of an audiovisual content, the audiovisual content being available from at least two servers in at least two versions corresponding respectively to different transmission bit-rates, the transmission of the audiovisual content being performed in successive parts, each of the successive parts being chosen as one of at least two versions in response to transmission requests sent by the apparatus, the transmission requests comprising a transmission parameter, the apparatus comprising:

a communication interface for sending information representative of the delivery of an audiovisual content from one of at least two servers, and for receiving a control parameter, the control parameter being defined from information representative of the delivery of an audiovisual content to the apparatus, a computing module to compute the transmission parameter of the transmission request from at least the control parameter.

According to an embodiment of the invention, the apparatus for receiving data comprises a memory for the storage of the control parameter and information representative of the delivery of the audiovisual content from one of at least two servers.

According to an embodiment of the invention, the apparatus for receiving data is a laptop equipment.

According to an embodiment of the invention, the apparatus for receiving data is a set-top box equipment.

According to an embodiment of the invention, the apparatus for receiving data is a mobile terminal.

The invention also concerns a controller apparatus to control the switching and transmission data rate between at least two servers and a receiver, the data being representative of an audiovisual content, the audiovisual content being available from each of at least two servers in at least two versions, the versions corresponding respectively to different transmission bit-rates, the at least two servers being adapted to transmit the audiovisual content in successive parts, each of the successive parts being chosen as one of at least two versions in response to transmission requests sent by a receiver, the transmission requests comprising a transmission parameter, the controller apparatus comprising:

a computing module to compute a control parameter from at least information, a communication interface, for receiving from the receiver an information representative of the delivery of an audiovisual content by one of at least two servers and to transmit the control parameter to the receiver.

According to an embodiment of the invention, the controller apparatus is located in a residential gateway equipment.

According to an embodiment of the invention, the controller apparatus is located in a Digital Subscriber Line Access Multiplexer equipment.

The invention also concerns a method in a receiver for receiving data from one of at least two servers, the data being representative of an audiovisual content, the audiovisual content being available from each of at least two servers in at least two versions, the versions corresponding respectively to different transmission bit-rates, the at least two servers being adapted to transmit the audiovisual content in successive parts, each of the successive parts being chosen as one of at least two versions in response to transmission requests sent by the receiver, the transmission requests comprising a transmission parameter, the method comprising the steps of:

transmission to a controller of information representative of the delivery of the audiovisual content to the receiver, reception from a controller of a control parameter, the control parameter being defined from the information representative of the delivery of the audiovisual content to the receiver, transmission to one of the at least two servers of a request comprising the transmission parameter defined from at least the control parameter.

According to an embodiment of the invention the step of reception of a control parameter further comprises a step of updating at least one reception parameter of the receiver.

BRIEF DESCRIPTION OF THE DRAWINGS

The invention will be better understood and illustrated by means of the following embodiment and execution examples, in no way limitative, with reference to the appended figures on which:

In FIGS. 1, 2, 3 and 4, the represented blocks are purely functional entities, which do not necessarily correspond to physically separate entities. Namely, they could be developed in the form of hardware or software, or be implemented in one or several integrated circuits.

DETAILED DESCRIPTION OF PREFERRED EMBODIMENTS

It is to be understood that the figures and descriptions of the present invention have been simplified to illustrate elements that are relevant for a clear understanding of the present invention, while eliminating, for purposes of clarity, many other elements found in typical digital multimedia content delivery methods and systems. However, because such elements are well known in the art, a detailed discussion of such elements is not provided herein. The disclosure herein is directed to all such variations and modifications known to those skilled in the art.

Figure 1:
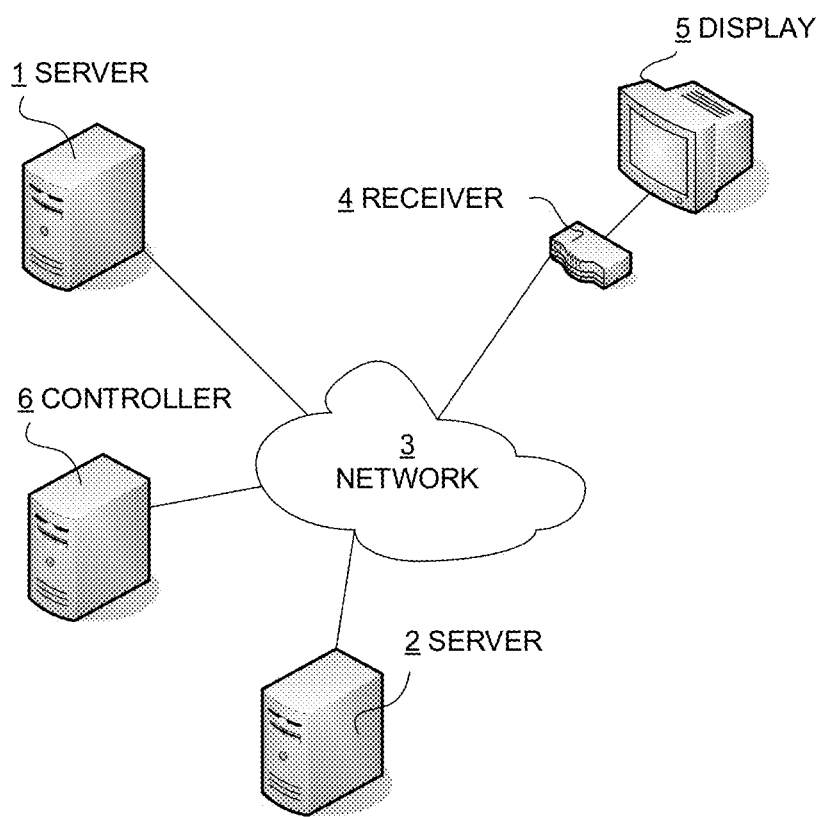
FIG. 1 illustrates an overall network architecture in which a CDN consumption control is made according to an embodiment of the invention.

The system according to the embodiment of the invention is represented in FIG. 1. It comprises a multipath adaptive streaming client device 4 also called a receiver, an adaptive streaming CDN server 1, an adaptive streaming CDN server 2 and a controller 6. The receiver 4 is connected to a network 3. The network 3 comprises a wide area network such as internet and a local area sub-network for the interconnection of the receiver 4.

The CDN servers 1 and 2 collaborate to deliver audiovisual content to the receiver 4 according to some requests sent by the receiver 4. The delivery of an audiovisual content from the CDN servers 1 and 2 to the receivers uses an HTTP adaptive streaming technique well known to the skilled in the art.

The receiver 4 is connected to a display apparatus 5 for the rendering of the audiovisual content received by using the multipath adaptive streaming method.

According to the embodiment, the receiver periodically (or repeatedly) sends to the controller 6 information related to the multipath adaptive streaming session in progress.

The term "periodically" means, in the following paragraphs, that the sending of information may correspond to a periodical sending or simply a sending which is made repeatedly without having a constant periodicity.

The receiver 4 periodically transmits information representative of the rendering (or quality of the rendering) to the controller 6, such as, for example, the amount of data received from each of the two CDN servers 1 and 2, the amount of data received from each CDN server during a predetermined interval of time, the filling level of the memory buffer used for the reception of the data representative of an audiovisual content received from each of the CDN server, the version of the audiovisual content part currently received (i.e.: low quality, medium quality, high quality or the corresponding bit-rates), the available size of the buffer, the number of reception buffer underflow (dry-out) or the number of reception buffer overflow during the adaptive streaming. It is well known by the one skilled in the art that the rendering, or more particularly the quality of the rendering of an audiovisual content by using the adaptive streaming, at a given time, is depending on (or related to) such information, characteristics or parameters of the receiver 4. Alternatively, only a part of the above-listed information is sent to the controller 6. Alternatively, the information transmitted by the receiver 4 to the controller 6 is any other information related to the receiver. It can be, for example, the number of times the receiver switches to another version of the audiovisual content during a time interval while receiving data from a CDN server; the number of version switching during the whole audiovisual content transmission; it can also be the amount of data during a time interval for each version of the audiovisual content.

More generally, any information representative of the network status seen from the receiver 4 (i.e.: available bandwidth, congestions) is relevant for the controller 6 in order to define if a receiver has good performances for rendering a streamed content or if a receiver have bad performances due to the network status between the CDN servers used and itself.

Alternatively, the information is the aggressiveness of the adaptive streaming algorithm which is defined as the ability to switch from a version (or quality) to another one of the audiovisual content. A low aggressiveness parameter makes the reception system conservative (with restricted switching capabilities) whereas a high aggressiveness parameter allows the receiver to switch more often from a content version to another one. The aggressiveness is a parameter of the adaptive streaming algorithm of a receiver according to the embodiment of the invention.

According to the information received from the receiver 4, the controller 6 determines (computes) if the receiver 4 is in good adaptive streaming conditions or if the receiver 4 is in poor conditions. Good conditions are defined as a rendering of an audiovisual content without interruption and with a medium or high quality. The poor conditions are defined as a rendering with interruption or always with the lower level of quality. The streaming conditions for the receiver 4 may depend on the network 3 and the use of the network 3 by some other receivers (not represented here) connected to the CDN servers 1 and 2.

Knowing the conditions of data reception, the controller 6 sends control parameters to the receiver 4 in order to adjust the use of the network 3. The controller 6 sends one or more control parameters to the receiver 4 by addressing the receiver individually through an unicast transmission. Alternatively, the controller 6 addresses a group of receivers comprising the receiver 4 by using, for example, a multicast transmission. The multicast transmission allows the addressing of many receivers connected to the CDN servers through the network 3 at the same time. The parameters can be determined, for example, in order to define the amount of data to be requested to the CDN server 1 and the amount of data to be requested to the CDN server 2. Advantageously, the control parameters can be defined in order to limit the reception buffer size of the receiver to receive the data from any of the CDN servers. The control parameter can also be defined to limit the quality of the requested version of a part of an audiovisual content from any of the CDN servers. In a variant of the embodiment, the control parameters are defined to adjust a reception parameter such as a parameter of the adaptive streaming algorithm of the receiver 4 (for example the aggressiveness).

More generally, a control parameter sent by the controller 6 to the receiver 4 can be a reception parameter or can be related to a reception parameter (i.e.: the ratio of data to be requested to the CDN server 1 and the ratio of data to be requested to the CDN server 2, the reception buffer size, the aggressiveness of the adaptive streaming algorithm). It can also be related to parameter of the requests (i.e.: the server identifier, the version of content, the bit-rate, the delivery speed of the server) sent from the receiver to any of the CDN servers 1 and 2.

The control of the ratio of data to be requested (and received) from the CDN server 1 and the ratio of data to be requested (and received) from the CDN server 2 is an easy way to control the whole behavior (for the delivery and the rendering of a content) of the streaming system.

According to the embodiment, the controller 6 sends the control parameters in some messages structured according to a remote control protocol such as, for example TR-069 (CPE WAN Management Protocol v1.1, Issue 1, Amendment 2, December 2007).

Based on the information received from the receiver 4, the controller 6, acting as a remote management server (or a remote controller) configures the receiver settings (for example the CDN server selection to get the next parts of the audiovisual content, the aggressiveness of the adaptive streaming algorithm, the buffer size, the maximum bit-rate required for data transmission) to monitor the quality of the received audiovisual content. According to the embodiment, the overall quality for the receiver 4 is computed by the controller 6 by considering the previously computed quality of the receiver 4 while receiving the data from each of the CDN servers.

More generally, the embodiment of the invention consists in a method to control transmission data rate between the CDN server 1 and the receiver 4 in one hand and the CDN server 2 and the receiver 4 in another hand. The CDN servers 1 and 2 are adapted to transmit data representative of audiovisual content. Each of the audiovisual content is available on the CDN server 1 and the CDN server 2 in at least two versions. The different versions of an audiovisual content correspond respectively to different transmission bit-rates. The CDN server 1 and the CDN server 2 are adapted to transmit the audiovisual content in successive parts (also called chunks). Each of the successive parts to be received by the receiver 4 is chosen between the available versions in response to transmission requests received by the CDN server 1 and the CDN sever 2.

According to a variant, the receiver 4 requests a part of a chunk from the CDN server 1 and a part of the same chunk from the CDN server 2 depending on a control parameter received from the controller 6. The receiver 4 is able to send a request to get a part of a chunk to any of the CDN servers before having received the response to a previous request for another part of the same chunk to another server. If the CDN server 1 fails to transmit a requested part of a chunk to the receiver 4 in a predetermined interval of time, the receiver 4 requests the same part of the chunk to the CDN server 2, and vice-versa.

A transmission request sent by the receiver 4 to any of the CDN servers to receive a part of audiovisual content from this CDN server comprises a transmission parameter such as, for example, the speed of data delivery or the version (corresponding to a given bit-rate).

The controller 6 periodically receives information from the receiver 4. Information is representative of the rendering of the audiovisual contents received and rendered by the receiver 4.

According to the information received from the receiver 4, the controller 6 computes some control parameters for some other receivers connected to the network 3 in order to find a better sharing of the overall bandwidth. According to the current sharing of the bandwidth at a given time, the sending of a control parameter can be done for one receiver only, for a group of receivers or for all receivers.

Information received by the controller 6 is, for example, the ratio of data received from a CDN server, reception memory buffer size, the number of switches from a version to another version of a received audiovisual content, the number of memory buffer underflow or overflow, the aggressiveness parameter of the adaptive streaming algorithm of the receiver.

By sending one or more control parameters a receiver connected to the network 3 (i.e.: the receiver 4), the controller 6 can force, for instance, the maximum size of the data reception buffer, the aggressiveness parameter of the adaptive streaming algorithm or the better quality that can be requested by a receiver to a CDN server upon a new adjustment (for a given interval of time).

Information from the receiver 4 to the controller 6 and the control parameters from the controller 6 to the receiver 4 are carried by the remote control protocol based on TR-069. The remote control protocol is an extension of the existing TR-069 protocol with some additional commands and parameters. Alternatively, the control parameters are carried by an extension of TR-069 protocol and the information representative of the rendering sent by the receiver to the controller 6 are carried based on one or more different protocols. In this case, the controller 6 is compatible with any of the different protocols used by the receivers to send the information.

Figure 2:
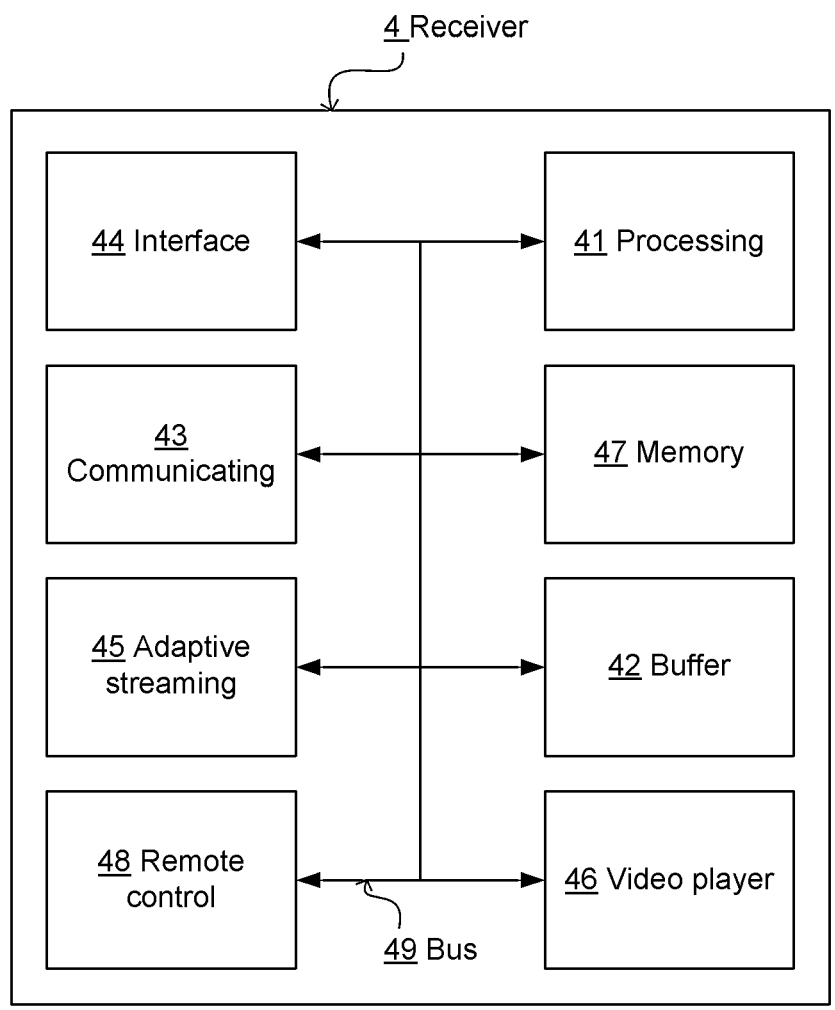
FIG. 2 illustrates a receiver as used in the network illustrated in FIG. 1.

The receiver 4 according to the embodiment of the invention is illustrated in FIG. 2. The receiver, also called an adaptive streaming client apparatus, comprises a communication interface 44 for connection to the network 3. The receiver comprises a communicating module 43 which comprises the protocol stacks to communicate to the CDN server 1, the CDN server 2 and the controller 6. In particular the communicating module comprises the TCP/IP stack well known in the art. Of course it can be any other type of network and/or communicating means enabling the adaptive streaming client to communicate with the CDN server 1, the CDN server 2 and the controller 6. According to the embodiment, a single communication interface is used to receive the control parameters and to send the information representative of the quality of the content transmission. According to a variant, two different communication interfaces are used. The receiver 4 also comprises an adaptive streaming module 45 which is a computing module. The computing module 45 is an HTTP streaming client that receives HTTP streaming content from the CDN server 1 and the CDN server 2. It continually selects the CDN server, and the chunk or the part of a chunk at the bit-rate that better matches the network constraints. A chunk is defined as a part of the received audiovisual content from the CDN server 1 or the CDN server 2, in a version corresponding to a given bit-rate as defined for the adaptive streaming. The receiver 4 receives the control parameters from the controller 6 thanks to the remote control module 48. The control parameters are stored in the buffer 42 and are readable from the adaptive streaming module 45 which is a computing module. The buffer 42 is also used to store the information representative of the rendering of audiovisual content. The information are written in the buffer 42 by the adaptive streaming module 45 and are read by the remote control module 48 to be send to the controller 6 through the communication interface. The receiver 4 comprises a video player 46 that is adapted to decode and render the received audiovisual content. The receiver 4 further comprises a processor 41 and a buffer 42. The processor 41 is used for executing the applications and programs stored in the receiver 4. The buffer 42, which is a memory or a part of a memory, is used for buffering the chunks (or parts of chunks) received from the CDN server 1 or the CDN server 2 before they are transmitted to the video player 46. In particular the memory is a volatile memory. The receiver 4 also comprises a non-volatile memory 47 for storing applications and programs running on the client. The receiver 4 could be a portable media apparatus (a mobile equipment) or a laptop.

All the above-cited modules of the receiver 4 are interconnected through an internal bus 49.

Alternatively the receiver 4 does not comprise a video player and comprises an interface to connect a video player. Then the receiver 4 is a video decoder such as a set-top box.

Figure 3:
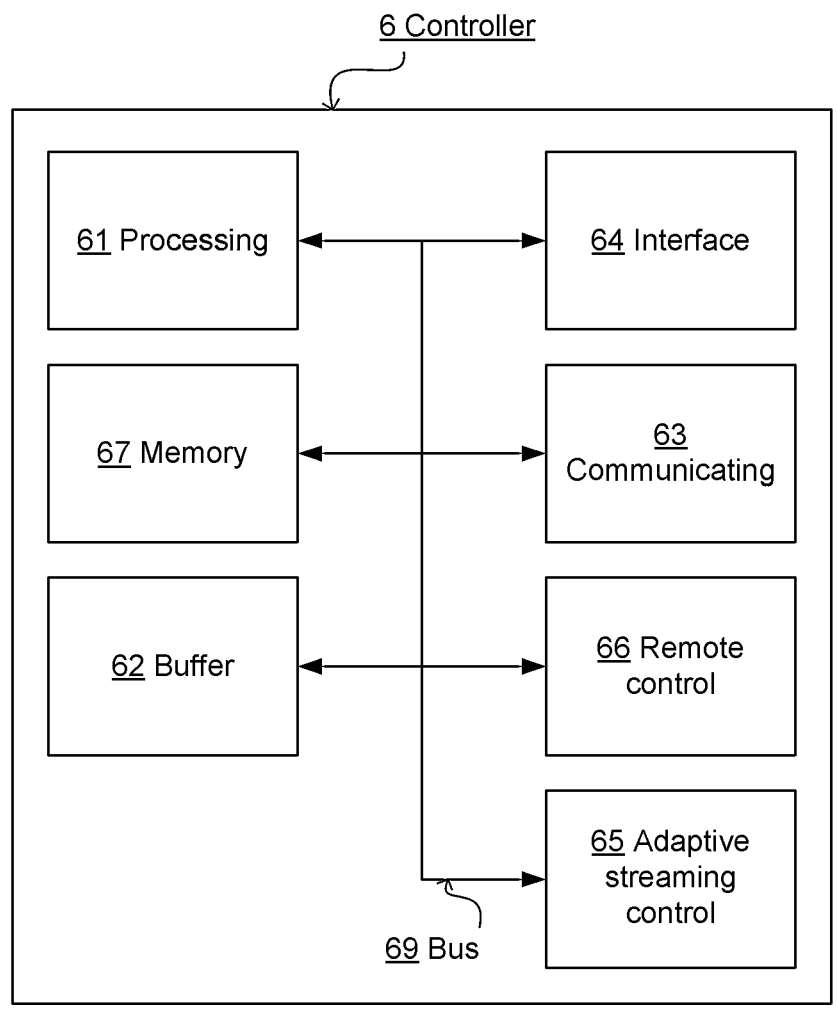
FIG. 3 illustrates a controller as used in the network illustrated in FIG. 1.

FIG. 3 illustrates the controller 6 of the adaptive streaming system according to the embodiment of the invention. The controller 6 comprises a communication interface 64 for connection to the network 3 and thus, for the communication with the receiver 4. Similarly to the receiver 4, the controller comprises a communicating module 63 which comprises the protocol stacks to communicate with the receivers (the adaptive streaming client). According to the embodiment, a single communication interface is used to receive the information representative of the quality of the streaming session and to send the control parameters. According to a variant of the embodiment, two different communication interfaces are used. The controller comprises a processing unit 21, memory module 67 and a buffer 62. The processing unit 61 is used for executing the applications and programs stored in the controller 6. The buffer 62, which is a memory or a part of a memory, is used for buffering the information and information messages received from the receiver 4 or any other receiver connected to the network 3 and the control messages (and parameters) to be sent to the receiver. The controller 6 also comprises a non-volatile memory 67 for storing applications and programs running on the controller. A remote control module 66 is used to handle the remote control protocol for the messaging between the controller and the receiver. The remote control comprises receiving information representative to the delivery (and thus the quality of the rendering) of the audiovisual content of the streaming session from the receiver and sending control parameters to force parameters of the receiver. The remote control module handles the remote control protocol based on TR-069 to receive and send messages from/to the receiver 4. The controller 6 further comprises an adaptive streaming module 25 which is a computing module for computing the control parameters to be sent to the receiver according to the received information (representative of the quality of the transmission and rendering of the audiovisual content on the receiver). All the above-cited modules of the controller 6 are interconnected through an internal bus 29.

Figure 4:
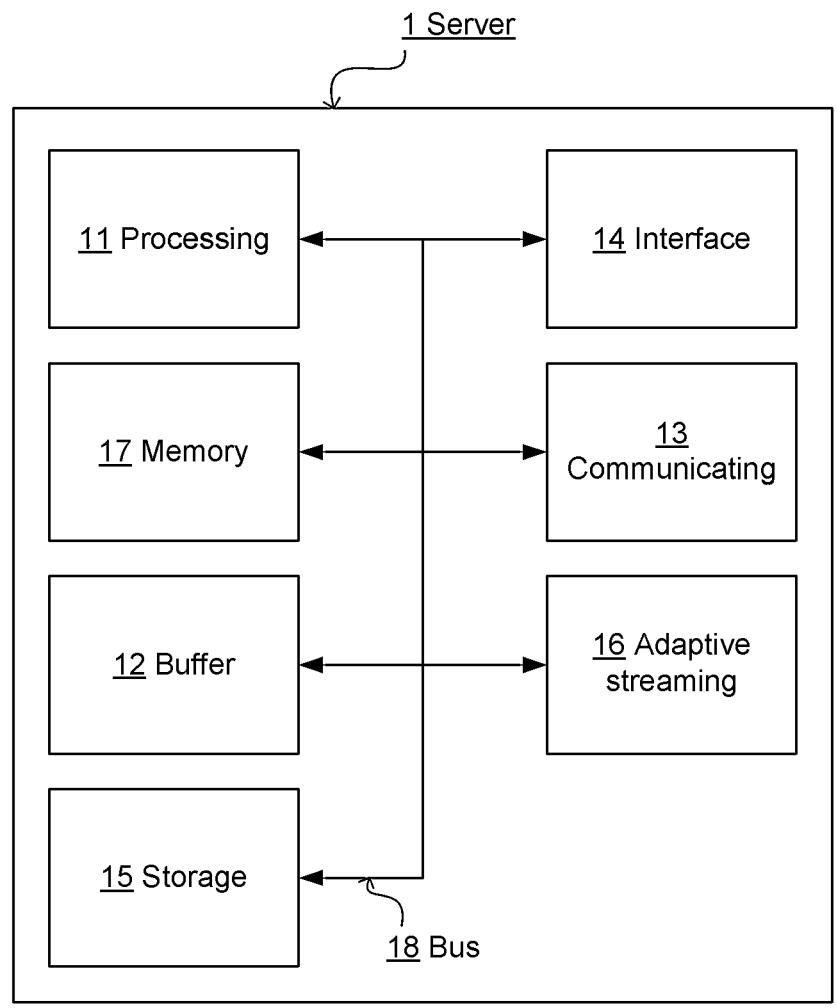
FIG. 4 illustrates a CDN server as used in the network illustrated in FIG. 1.

FIG. 4 illustrates the adaptive streaming CDN server 1. The CDN server 1 comprises a communication interface 14 to connect to the network 3 and to communicate with the receiver 4. The communicating module 13 comprises the protocol stacks, such as, for example the TCP/IP stack. The processing unit 11 executes the applications and routines of the CDN server 1. The non-volatile memory 17 comprises the software and application to be executed by the processing unit 11 and the memory buffer 12 is a volatile memory for data storage during the execution of the application. The buffer 12 is also used for the storage of messages from the receivers including those related to the adaptive streaming (requests). The storage module 15 comprises a media for the storage of all the audiovisual contents to be delivered to the receiver 4. The storage module 15 comprises all the versions (corresponding to different bit-rates) for each of the audiovisual content. A version of an audiovisual content can be stored either as single file or can be concatenated with other versions in a file. The audiovisual content can be audio content, video content or both. The adaptive streaming module 16 is in charge of handling the incoming messages from the receiver 4 for the adaptive streaming of any content stored on the storage module 15. The adaptive streaming module 16 delivers the manifest file corresponding to an audiovisual content and handles the incoming requests from the receivers. It interprets the parameters of the request and delivers the corresponding part of the content (chunk or part of chunk) to the receiver through the communication interface 14. All the above-cited modules of the CDN server 1 are interconnected through an internal bus 18.

The CDN server 2 has a similar architecture as the CND server 1.

So, the CDN server 1 (illustrated by FIG. 4), the CDN server 2, the controller 6 (illustrated by FIG. 3) and the receiver 4 (illustrated by FIG. 2) constitute the overall multipath adaptive streaming system of the invention according to the embodiment.

Herein-after is an example of the initialization of an adaptive streaming session and how the overall system interacts according to the embodiment.

The control of the essential parameters of the multipath adaptive streaming is realized through the usage of a manifest file (comprising a playlist) that a receiver downloads first when initiating an adaptive streaming session. The manifest file contains for example the duration of a chunk, the number of versions (or quality, or bit-rates) each chunk has been encoded, the size of the file, the video format (such as, for example MPEG2-TS or MPEG4) and the list of other CDN servers that may deliver the same audiovisual content.

The adaptive streaming proposes a continuous streaming between the CDN server 1, the CDN server 2 and the receiver 4 without any interruption but with a video quality that degrades when network congestion occurs and upgrades when the congestion disappears. Depending on the network conditions between the CDN server 1 and the receiver 4 in one hand and the CDN server 1 and the receiver 4 in another hand, the controller sends control parameter to define the ratio of data to be received by the receiver 4 from each of the CDN servers 1 and 2. A video file or stream is encoded several times targeting different bit-rates and is stored on the storage module 15 of the CDN server 1 and CDN server 2. The encoding is for example MPEG2-TS (ISO/IEC 13818-1). or H264 (ISO/CEI 14496-10). Each file is split into chunks of the same duration (for example 2 seconds) forming micro files set. All micro files set (one set per bit-rate) are stored in a single HTTP server. A HTTP server is implemented by the CDN servers 1 and 2. Regularly, (for example every 2 seconds), the receiver 4 that downloads an audiovisual content estimates the available bandwidth with the each of the CDN servers 1 and 2. The adaptive streaming module 44 of the receiver requests accordingly the content part (chunk or part of chuck) encoded with the corresponding bit-rate and feeds the decoder of the video player 46 progressively. According to the embodiment of the invention, the control protocol and ultimate transport protocol is HTTP. Alternatively, it can be RTSP.

Beside the manifest file, the adaptive streaming module 44 of the receiver 4 gathers several control parameters that are necessary to finely tune the system and that influences the way the network 3 is used. It comprises the algorithm for selecting the server, smoothing the degradation/upgrade of the video quality depending on the network status (for example the congestions and the overall bandwidth). The adaptive streaming algorithm of the adaptive streaming module 45 of the receiver may operate several approaches ranging from the most conservative to the most aggressive. The mode of operation directly impacts the user experience and the network 3 usage.

The use of the controller 6 to define some control parameters of the receiver 4, including transmission parameters of the requests to the CDN servers 1 and 2, brings the ability to configure some parameters of an adaptive streaming client that have an impact on the end user experience but also on the network 3 traffic and therefore on the overall system performance.

The control parameters sent from the controller 6 to the receiver 4 may be different depending on the network status. The controller may send a parameter to limit the size of the reception buffer to receive data from a first server (i.e.: the CDN server 1) and a parameter to limit the bit-rate of the adaptive streaming session to receive data from a second server (i.e.: the CDN server 2). In addition, the controller can send to the receiver 4 two successive control parameters related to the same server. For example, the controller can send a control parameter to the receiver 4 to limit the bit-rate of the streaming session from the server 1 and then send a control parameter to the receiver 4 to limit the speed delivery factor of the data to be received from the sever 1. The controller 6 computes the received information from the receiver 4 and selects the parameters to be set accordingly (at the receiver's side). It also defines the values of these parameters.

The controller 6 defines relevant control parameters (and their corresponding values) for the receiver 4. This is made according to the status information periodically received from the receiver 4. The controller 6 then remotely configures the receiver 4. The controllers 6 "observes" and monitors the impact of each of the servers used on the end user received quality for the receiver. After the computation of information received from the receiver, the controller 6 determines the optimal system configurations and sends control parameter to the receiver. It can be send to some other compatible receivers if necessary.

Herein-after is an example of how the controller 6 monitors the overall performance of the adaptive streaming between the adaptive streaming CDN server 1, the adaptive streaming CDN server 2 and the receiver 4 through the network 3:

An accurate monitoring information is collected by the receiver 4 for each adaptive streaming session in progress with the CDN server 1 and the CDN server 2. When CDN server 1 and CDN server 2 are used in collaboration to deliver a same streaming content, the receiver 4 collects information for each considered interval of time such as for example the reception of a part of the audiovisual content. The collected information is typically how many bytes have been received from each of the CDN server 1 and the CDN server 2. The collected information is then sent to the controller 6 by the receiver 4. According to a variant of the embodiment, the collected information is sent to the controller 6 upon request of the controller 6 to the receiver 4.

Information is stored locally on the receiver 4 and can be queried by the controller 6 that is then able to compute the amount of data that has been delivered by each of the CDN servers.

The controller 6 determines the respective loads of each of the CDN servers used and the network conditions between each of the CDN servers 1 and 2 and the receiver 4. The controller 6 also computes some control parameters to send to the receiver 4 such as the maximum ratio of data to be requested to a CDN server or the maximum bit-rate (corresponding to a version of the audiovisual content) to be requested to a CDN server.

The receiver 4 receives the control parameters from the controller 6 and sends the next requests to the servers accordingly.

More generally, in the above-cited example of the adaptive streaming system illustrated on the FIG. 1, the controller 6 controls the transmission data rate between the CDN server 1 and the receiver 4 and the transmission data rate between the CDN server 2 and the receiver 4. The CDN servers are adapted to transmit the data representative of the audiovisual contents. The audiovisual content is available from the CDN server 1 in different versions and is also available from the CDN server 2 in different versions. The available versions of the audiovisual content correspond to different transmission bit-rates. The CDN servers are adapted to transmit the audiovisual content in successive parts. Each of the successive parts of the audiovisual content is chosen by the receiver by transmitting a request to the CDN server 1 or the CDN server 2 comprising a transmission parameter (such as the version (bit-rate) or a delivery speed). The controller 6 receives periodically information reported from the receiver 4. Information from the receiver 4 is representative of the transmission (an thus the rendering) of the audiovisual contents. A low bit-rate brings a low quality of rendering for the end used whereas a high bit-rate brings a high quality of rendering.

Figure 5:
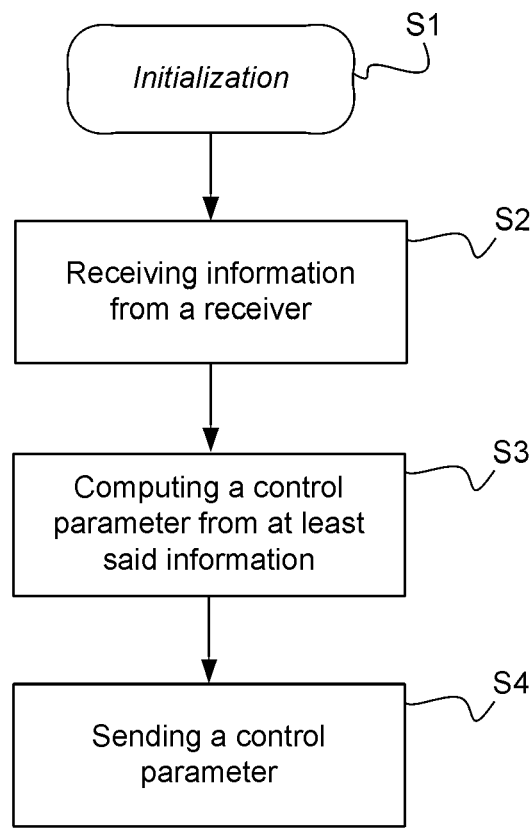
FIG. 5 is a diagram illustrating a method in the controller of FIGS. 1 and 3 according to an embodiment of the invention.

FIG. 5 is a diagram illustrating the method in the controller 6 according to the embodiment.

The step S1 is the initialization of the adaptive streaming system. The receiver 4 sends requests to the CDN server 1 and the CDN server 2 and initializes two adaptive streaming sessions in order to download and to achieve the rendering of an audiovisual content in a multipath way from the CDN server 1 and the CDN server 2. The receiver 4 receives the successive parts of the audiovisual content from at least two servers. At step S2, the receiver 4 reports to the controller 6 information representative to the delivery and rendering of the received part from the CDN server 1 and information representative to the delivery and rendering of the received part from the CDN server 2. The received part from any of the CDN servers can be either chucks or part of chunks.

Based on the information received from the receiver 4, the controller 6 evaluates the overall performance of the adaptive streaming system and computes at step S3, at least a control parameter, such as the ratio of the data representative of the audiovisual content to be requested to the CDN server 1 and the ratio of data to be requested to the CDN server 2.

The controller 6 then sends at least a control parameter to the receiver 4 in order to configure the receiver and to have a better sharing of the available bandwidth of the network 3.

Advantageously, the method according to the embodiment forces the configuration of the receiver 4 or a group of receivers comprising the receiver 4 to limit their requested use of bandwidth for a CDN server and to use more available bandwidth from other CDN servers.

Figure 6:
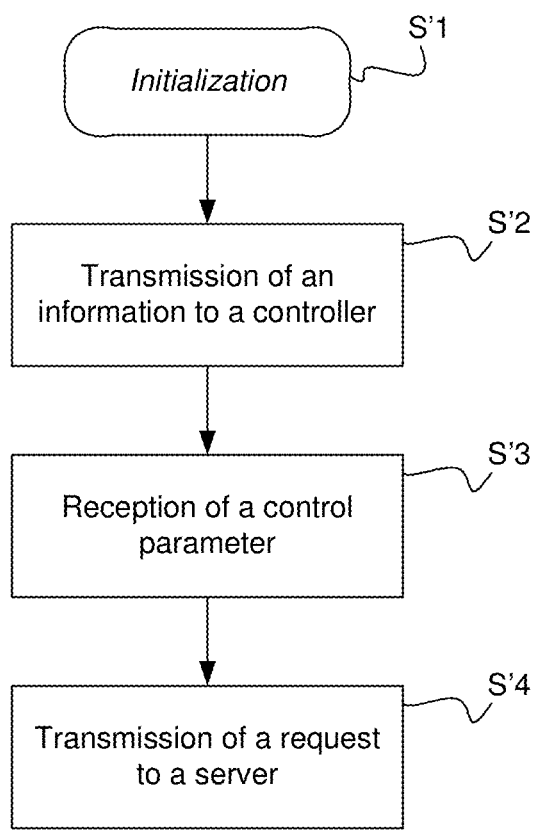
FIG. 6 is a diagram illustrating a method in a receiver as represented in FIG. 1 and FIG. 2, according to an embodiment of the invention.

FIG. 6 is a diagram illustrating the method at the receiver 4 according to the embodiment of the invention.

At step S'1, the receiver initializes a multipath adaptive streaming session with the CDN server 1 and the CDN server 2 and starts to receive an audiovisual content from both servers.

At step S'2, after the reception of the first parts of the audiovisual content (chunks or parts of chunks) partially received from the server 1 and partially received from the server 2, the receiver 4 reports to the controller 6 one or more information representative of the delivery and the rendering of the audiovisual content comprising information related to each of the CDN servers 1 and 2. The information is for example reported to the controller every minute. The control computes the information received from the receiver 4 and sends a control parameter to the receiver 4. This control parameter is received by the receiver at step S'3.

At step S'4 the receiver sends a request to get the next part (chunk or part of chunk) of audiovisual content comprising a transmission parameter such as the server identifier, the version of the audiovisual content or the delivery speed by the selected server. The transmission parameter of the request is defined according to the control parameter previously received from the controller 6. For example, the control parameter indicates to the receiver for the next parts of the audiovisual content that 60% of the data must be requested to the CDN server 1 and 40% of the data must be requested to the CDN server 2.

Advantageously, the controller 6 is adapted to adjust the ratio of data received from the server 1 and the ratio of data received from the server 2 in order to have a fair delivery of audiovisual content.

The ability for the receiver 4 to receive some successive parts of a streamed audiovisual content from different servers (under control of the controller 6) is defined in the present description as a method to control the "switching" between the two CDN servers 1 and 2.

In other words, the term "switching" (between many servers) defines the ability for the receiver 4, under control of the controller 6, to get each successively part of the downloaded audiovisual content from any of the two CDN servers.

Some examples of data model for the control messages carrying control parameters from the controller 6 to the receivers using an extension of the TR-069 protocol is given below:

.STBService.{i}.Components.FrontEnd.{i}.IP.Multipath-AdaptiveStreaming.

| Control Parameter | Read/ Write | Description |
| --- | --- | --- |
| MaxDataRatio (DCN server) | W | Maximum percentage of data of an audiovisual content to be requested to a specific DCN server from the receiver. |
| MaxBuffer (DCN server) | W | Maximum amount of data in Bytes the client is allowed to store in advance of the current the play out. A large buffer gives more time to the client for adapting to changing quality of service, but will waste network bandwidth if the user stops or changes to another audiovisual content. |
| MaxDataRateRatio (DCN server) | W | Percentage of the maximum data rate the client shall not exceed when downloading data. It shall be greater than 100. For instance if the maximum data rate of a stream is 8 Mbit/s, and if MaxDataRateRatio is set to 150, then the client shall always download data at a rate lower than 12 Mbit/s. |

The invention is not limited to the embodiment described herein-above. Particularly the invention also concerns a method to control the adaptive streaming between many servers and a field of receivers. According to a variant, the controller predefines the parameters for some groups of receivers within the field of receivers and then controls some of the receivers individually according to the information received.

According to another variant, the controller first uses a random algorithm to define the control parameters, initialize the receivers, and then controls some of the receivers according to the information received.

According to another variant, the controller controls the receivers by addressing some groups of receivers and redefines the groups periodically.

Advantageously, the controller gives priority or privileges to some of the receivers. It can be done, for example, according to a level of subscription to a service provider or depending on the expected level of the quality of the rendering for a subset of the receivers (HD quality versus normal quality, for example).

The invention also concerns any system of multipath adaptive streaming adapted to deliver some content from at least two servers and a receiver. Advantageously, the audiovisual content comprises any kind of content such as text, maps, music, video, meta-data, binary data (i.e.: executable application).

The invention concerns generally data receivers. It comprises apparatus such as set-top boxes, gateways including an audio/video decoder, laptop, and mobile equipments (mobile phone, personnel assistants, positioning systems).

Reference herein to "one embodiment" or "an embodiment" means that a particular feature, structure, or characteristic described in connection with the embodiment can be included in at least one implementation of the invention. The appearances of the phrase "in one embodiment" in various places in the specification are not necessarily all referring to the same embodiment, nor are separate or alternative embodiments necessarily mutually exclusive of other embodiments.

Reference numerals appearing in the claims are by way of illustration only and shall have no limiting effect on the scope of the claims.

The invention claimed is:

1. A method, to be performed in a controller, to control a transmission in successive parts of audiovisual content to a receiver, said audiovisual content being available in at least two versions from at least one server, said server and said receiver being remote from said controller, said versions corresponding respectively to different transmission bit-rates, each of said successive parts being chosen as a part of one of said two versions in response to transmission requests sent by said receiver, said method comprising:
   receiving, by the controller, information representative of a previous delivery to said receiver of at least one first part of said successive parts of audiovisual content; and
   transmitting, by the controller, a control parameter to said receiver, said control parameter being computed based at least partially on said received information and adapted to be used by said receiver in order to compute at least one transmission parameter to be comprised in a transmission request relating to at least one second part of said successive parts of audiovisual content.

2. The method according to claim 1, wherein said information comprises at least one of the following parameters:
   a server identifier,
   a receiver identifier,
   an identifier of a group of receivers which comprises said receiver,
   a positioning information of said receiver,
   a data transmission bit-rate between a server and said receiver,
   a size of a data reception buffer of said receiver,
   a quality indicator of a delivery of said audiovisual content to said receiver,
   a number of times said receiver switches from one of said versions to another one of said versions during a given time interval while receiving said audiovisual content,
   a number of bytes received by said receiver during a predefined time interval, a number of bytes received by said receiver during a predefined time range for each of said at least two versions of said audiovisual content.

3. The method according to claim 1, wherein said control parameter comprises at least one of the following parameters:
a server identifier,
a maximum value of bit-rate to be requested,
a list of allowed versions of said versions to be requested,
a maximum size of reception buffer,
a maximum speed factor to be indicated within said request,
a parameter of an adaptive streaming algorithm of said receiver.

4. A receiver apparatus for receiving audiovisual content in successive parts, said audiovisual content being available from at least one server in at least two versions corresponding respectively to different transmission bit-rates, each of said successive parts being chosen as a part of one of said at least two versions in response to transmission requests sent by said receiver apparatus, said transmission requests comprising a transmission parameter, said receiver apparatus further comprising:
a communication interface;
at least one processor configured to:
send to a remote controller apparatus information representative of a delivery, to said receiver apparatus, of at least a first part of said successive parts of audiovisual content that has been previously received by said receiver apparatus;
receive a control parameter, said control parameter being defined from said information representative of the delivery of said first part; and
compute said transmission parameter of said transmission request from at least said control parameter; and
transmit a transmission request relating to at least one second part of said successive parts of audiovisual content and comprising said transmission parameter computed from at least said control parameter.

5. The receiver apparatus according to claim 4, comprising a memory for storage of said control parameter and said information representative of the delivery of said first part of said audiovisual content from a server.

6. The receiver apparatus according to claim 4, wherein it is a laptop equipment.

7. The receiver apparatus according to claim 4, wherein it is a set-top box.

8. The receiver apparatus according to claim 4, wherein it is a mobile terminal.

9. The receiver apparatus according to claim 4, wherein said information comprises at least one of the following parameters:
a server identifier,
a receiver identifier,
an identifier of a group of receivers which comprises said receiver,
positioning information of said receiver,
a data transmission bit-rate between a server and said receiver,
a size of a data reception buffer of said receiver,
a quality indicator of a delivery of said audiovisual content to said receiver,
a number of times said receiver switches from one of said versions to another one of said versions during a given time interval while receiving said audiovisual content,
a number of bytes received by said receiver during a predefined time interval,
a number of bytes received by said receiver during a predefined time range for each of said at least two versions of said audiovisual content.

10. The receiver apparatus according to claim 4, wherein said control parameter comprises at least one of the following parameters:
a server identifier,
a maximum value of bit-rate to be requested,
a list of allowed versions of said versions to be requested,
a maximum size of reception buffer,
a maximum speed factor to be indicated within said request,
a parameter of an adaptive streaming algorithm of said receiver.

11. A controller apparatus to control a transmission in successive parts of audiovisual content to a receiver said audiovisual content being available in at least two versions from at least one server, said server and said receiver being remote from said controller, said versions corresponding respectively to different transmission bit-rates, each of said successive parts being chosen as a part of one of said at least two versions in response to transmission requests sent by said receiver, said controller apparatus comprising:
a communication interface;
at least one processor configured to:
receive, via the communication interface, an information representative of a previous delivery to said receiver, of at least a first part of said successive parts of audiovisual content;
compute a control parameter based at least partially on said received information and adapted to be used by said receiver in order to define at least one transmission parameter to be comprised in a transmission request relating to at least one second part of said successive parts of audiovisual content; and
transmit said control parameter to said receiver.

12. The controller apparatus according to claim 11, wherein it is located in a residential gateway equipment.

13. The controller apparatus according to claim 11, wherein it is located in a Digital Subscriber Line Access Multiplexer equipment.

14. The controller apparatus according to claim 11, wherein said information comprises at least one of the following parameters:
a server identifier,
a receiver identifier,
an identifier of a group of receivers which comprises said receiver,
positioning information of said receiver,
a data transmission bit-rate between a server and said receiver,
a size of a data reception buffer of said receiver,
a quality indicator of a delivery of said audiovisual content to said receiver,
a number of times said receiver switches from one of said versions to another one of said versions during a given time interval while receiving said audiovisual content,
a number of bytes received by said receiver during a predefined time interval,
a number of bytes received by said receiver during a predefined time range for each of said at least two versions of said audiovisual content.

15. The controller apparatus according to claim 11, wherein said control parameter comprises at least one of the following parameters:
a server identifier,
a maximum value of bit-rate to be requested, a list of allowed versions of said versions to be requested,
a maximum size of reception buffer,
a maximum speed factor to be indicated within said request,
a parameter of an adaptive streaming algorithm of said receiver.

16. A method to be performed in a receiver, for receiving audiovisual content in successive parts, said audiovisual content being available in at least two versions from at least one server, said versions corresponding respectively to different transmission bit-rates, each of said successive parts being chosen as a part of one of said at least two versions in response to transmission requests sent by said receiver, said transmission requests comprising a transmission parameter, said method comprising:
   transmitting, by the receiver, to a remote controller apparatus information representative of a previous delivery to said receiver of at least a first part of said successive parts of audiovisual content;
   receiving, by the receiver, a control parameter, said control parameter being defined from said information representative of the previous delivery of the at least first part of said audiovisual content;
   computing, by the receiver, said transmission parameter of said transmission request from at least said control parameter; and
   transmitting, by the receiver, a transmission request relating to at least one second part of said successive parts of audiovisual content and comprising said transmission parameter computed from at least said control parameter.

17. The method according to claim 16 wherein receiving a control parameter comprises updating, by the receiver, at least one reception parameter of said receiver.

18. The method according to claim 16, wherein said information comprises at least one of the following parameters:
   a server identifier,
   a receiver identifier,
   an identifier of a group of receivers which comprises said receiver,
   positioning information of said receiver,
   a data transmission bit-rate between a server and said receiver,
   a size of a data reception buffer of said receiver,
   a quality indicator of a delivery of said audiovisual content to said receiver,
   a number of times said receiver switches from one of said versions to another one of said versions during a given time interval while receiving said audiovisual content,
   a number of bytes received by said receiver during a predefined time interval,
   a number of bytes received by said receiver during a predefined time range for each of said at least two versions of said audiovisual content.

19. The method according to claim 16, wherein said control parameter comprises at least one of the following parameters:
   a server identifier,
   a maximum value of bit-rate to be requested,
   a list of allowed versions of said versions to be requested,
   a maximum size of reception buffer,
   a maximum speed factor to be indicated within said request,
   a parameter of an adaptive streaming algorithm of said receiver.

* * * * *